United States Patent [19]
Lisenbee et al.

[11] 3,993,075
[45] Nov. 23, 1976

[54] DISPOSABLE, DEFROSTABLE CRYOSURGICAL PROBE

[75] Inventors: Wayne F. Lisenbee, Simi; Keith E. Nelson, Los Angeles, both of Calif.

[73] Assignee: Dynatech Corporation, Burlington, Mass.

[22] Filed: Dec. 24, 1975

[21] Appl. No.: 644,162

[52] U.S. Cl................................. 128/303.1; 62/293
[51] Int. Cl.²........................................ A61B 17/36
[58] Field of Search..................... 62/293; 128/303.1

[56] References Cited
UNITED STATES PATENTS

| | | | |
|---|---|---|---|
| 3,477,434 | 11/1969 | Hood, Jr. et al. | 128/303.1 |
| 3,910,278 | 10/1975 | Crandell et al. | 128/303.1 |
| 3,951,152 | 4/1976 | Crandell et al. | 128/303.1 |

*Primary Examiner*—Channing L. Pace
*Attorney, Agent, or Firm*—Cesari and McKenna

[57] ABSTRACT

A small, disposable cryosurgical probe having a self-contained liquid refrigerant supply can be operated in either a freeze mode or a defrost mode. During the freeze mode the refrigerant is conducted from the supply to the probe tip as a two phase fluid so that the probe can freeze tissue for a relatively long period with a limited refrigerant supply. To facilitate detaching the probe tip from tissue, a button on the probe is depressed which switches the probe to its defrost mode of operation wherein room temperature liquid refrigerant is conducted directly from the supply to the probe tip thereby immediately warming the tip. The probe may be cycled several times between its freeze and defrost modes before the refrigerant supply is exhausted.

7 Claims, 3 Drawing Figures

DISPOSABLE, DEFROSTABLE CRYOSURGICAL PROBE

BACKGROUND OF THE INVENTION

This invention relates to a cryosurgical probe. It relates more particularly to a relatively low cost, self-contained probe particularly suited for operations involving the eye.

In probes of this general type, fluid is circulated through the probe tip to maintain the tip at a very low temperature, e.g., −30° C. When the probe tip is brought into contact with human tissue, the tissue at the point of contact becomes frozen and adheres to the tip. Thus if the probe is withdrawn, the adhered tissue is pulled away with it. Thus in a cataract removal operation, for example, the patient's eye lens becomes adhered to the probe and is extracted.

There are in use today various self-contained probes which carry their own refrigerant supply. Basically these units consist of a housing containing a reservoir of a suitable refrigerant such as Freon gas maintained as a liquid under high pressure. When it is desired to use the probe, the reservoir is opened allowing the refrigerant therein to flow to the probe tip where the refrigerant evaporates and, in the process, cools itself and the tip.

A particularly desirable disposable probe of this type is disclosed in U.S. Pat. No. 3,910,278. That probe is able to operate consistently for a relatively long period of time, e.g. 3 to 5 minutes on a moderately sized supply of refrigerant, e.g. 3 gm. This is because it maintains two phase flow of refrigerant to the probe tip. That is, the refrigerant flows through a capillary tube to the probe tip as a saturated vapor and liquid so that cooling at the tip is caused primarily by evaporation of the refrigerant right at the working end of the tip.

As described in detail in that patent, this two-phase flow is achieved by isolating and insulating the refrigerant flowing through the capillary tube from the cold gas exhausting from the probe tip thereby inhibiting regenerative cooling of the incoming refrigerant. Preferably this is accomplished by bathing the capillary tube through which refrigerant flows to the probe tip in room temperature liquid refrigerant. Since the specific volume of the fluid flowing to the tip is kept relatively high in this manner, the tip can be maintained at its −30° C working temperature for as long as 3 to 5 minutes, which is quite long enough for a cataract removal or removal of foreign material from the vitreous humor.

With probes of this type, it is desirable to be able to warm the probe tip following completion of surgical procedure in order to facilitate separating the tip from the tissue to which it is adhered. One probe of which we are aware (described in U.S. Pat. No. 3,524,446) accomplishes this by flooding the probe tip with liquid refrigerant maintained at room temperature. However, that probe requires several separate valves to enable the probe to operate properly in both its freeze and defrost modes. Furthermore, that probe must carry a relatively large supply of refrigerant, e.g. 10 to 12cc in order to adequately cool the tip for the required time during the freeze mode and yet have sufficient refrigerant left to warm the tip during the defrost mode. Accordingly the probe itself is rather large and unwieldy.

These prior disposable probes having a defrost capability are also disadvantaged because they are relatively complex and difficult to make due to the valving required. Consequently, they are relatively expensive considering that they are intended to be throw-away items.

SUMMARY OF THE INVENTION

Accordingly this invention aims to provide an improved disposable cryosurgical probe having a defrost capability.

Another object of this invention is to provide a probe of this general type which is relatively simple in its makeup.

A further object of the invention is to provide a disposable cryosurgical probe which is small, lightweight and easy to handle.

Yet another object of the invention is to provide a defrostable, disposable cryosurgical probe with a relatively limited refrigerant supply which may be cycled between its freeze and defrost modes of operation.

A further object of the invention is to provide a defrostable, disposable probe of this general type which requires only a relatively small volume of refrigerant.

Other objects will in part be obvious and will in part appear hereinafter.

The invention accordingly comprises the features of construction, combination of elements, and arrangement of parts which will be exemplified in the following detailed description, and the scope of the invention will be indicated in the claims.

Briefly, the present probe consists of a thin, pencil-like housing containing a cylindrical cartridge filled with a suitable pressurized refrigerant such as liquid Freon. The refrigerant is maintained at room temperature and is retained within the cartridge by a suitable fluid-tight seal.

The probe tip is positioned in the end of the housing opposite the cartridge. It consists of a relatively small diameter metal tube having one and secured within the housing and having its other end projecting from the housing, the exterior end of the tube being closed.

A tubular member positioned within the housing has one end extending into the cartridge somewhat, a sliding seal being provided between that member and the cartridge wall. The opposite end of the tubular member communicates with a passage through a valve manifold in the housing to be described in detail later.

A long length of capillary tubing is coiled up inside the tubular member, the end of the capillary tubing nearest the cartridge being open. The tubing extends from the tubular member, through a passage in the valve manifold and into the hollow probe tip, almost to its closed end. A fluid-tight seal is provided at the point where this inlet tube exits the manifold passage so that normally the interior of the probe tip is isolated from the interior of the tubular member and manifold passage.

A length of larger diameter capillary tubing functioning as a refrigerant exhaust tube extends from the valve manifold into the probe tip, terminating at a point near its closed end. Extending transversely through the valve manifold is a general cylindrical valve chamber. The manifold passage and the end of the exhaust tube in the manifold communicate with that chamber at different points along the length of the chamber. Also a refrigerant exhaust passage is provided at the end of the chamber nearest the exhaust tube, the exhaust passage leading ultimately to the atmosphere.

A valve member is slidably mounted within the valve chamber, the member having a portion projecting from the probe housing so that the valve member can be moved manually between two operative positions that place the probe in its freeze and defrost operating modes. In the "freeze" position toward which the valve member is biased, the end of the exhaust tube inside the manifold communicates with the exhaust passage and both of these conduits are isolated from the manifold passage. In the "defrost" position of the valve member, the manifold passage communicates with the end of the exhause tube in the manifold, both of those conduits, in turn, being isolated from the exhaust passage.

As described in U.S. Pat. No. 3,910,278, the refrigerant cartridge which is slidably mounted in the housing can be moved axially toward the tubular member by depressing a push button projecting from the upper end of the probe. The tubular member thereupon breaks the cartridge seal allowing refrigerant to flow into the tubular member thereby immersing the coiled capillary tubing therein in room temperature refrigerant.

In the present probe, since the tubular member communicates with the manifold passage and the portion of the valve chamber isolated by the valve member, those spaces also are always filled with room temperature refrigerant. If the valve member is in its freeze position, refrigerant can only flow from the tubular member through the inlet tube to the probe tip.

The refrigerant issues from the end of the inlet tube adjacent the working end of the probe tip and evaporates and expands and, becoming cold in the process, thereby directly cools the probe tip. The refrigerant then exhausts to the atmosphere as a gas, flowing through the exhaust tube and manifold exhaust passage which are in communication when the valve member is in that position. The working end of the probe tip is thus brought to its operating temperature very quickly because the cooling process does not depend upon thermal conduction along the probe tip. Rather the refrigerant is delivered directly to the working end of the tip.

Furthermore, the probe is able to operate consistently for a relatively long period of time, e.g. 3 to 5 minutes on a moderate amount of refrigerant contained inside the cartridge, e.g. 2.82cc of which 3 gm. is liquid at room temperature. This is because the immersion of the inlet tube in room temperature liquid refrigerant maintains two-phase flow of refrigerant all the way through the inlet tube to the probe tip. Thus the refrigerant flows through the inlet tube as a saturated vapor and liquid with a relatively high specific volume. Consequently, the probe tip can be maintained at $-30°$ C working temperature for that entire duration.

When it is desired to warm the probe tip, the valve member is moved to its defrost position whereupon the room temperature liquid refrigerant inside the tubular member and manifold passage is conducted into the exhaust tube where it flows in reverse through that tube flooding the interior of the probe tip. Since the exhaust tube is isolated from the manifold exhaust passage at this point, the pressurized refrigerant remains at room temperature thereby rapidly warming the tip.

Should the doctor then wish to cool the probe tip again, he simply releases the valve member which returns to its normal freeze position so that the exhaust tube is once more in communication with the manifold exhaust passage leading to the atmosphere. Immediately, there is a rapid drop in pressure inside the probe tip with the result that the liquid refrigerant therein immediately flashes to a vapor. The rapid expansion and evaporation of the refrigerant in the tip drastically cools the refrigerant and thereby recools the probe tip quickly to its operating temperature.

Thus the present disposable probe requires only a single valve to permit the probe to operate in both freeze and defrost modes. Accordingly, it is relatively inexpensive to make as compared with prior multivalved disposable probes having that capability as represented by the one depicted in U.S. Pat. No. 3,524,446.

Furthermore, the present probe still has the advantage of being able to operate for a relatively long period of time on a limited refrigerant supply. Consequently the probe is quite small and lightweight as compared with conventional defrostable, disposable probes which operate differently and thus require a larger refrigerant supply.

BRIEF DESCRIPTION OF DRAWING

For a fuller understanding of the nature and objects of the invention, reference should be had to the following detailed description taken in connection with the accompanying drawing, in which.

DESCRIPTION OF THE PREFERRED EMBODIMENT

Figure 1:
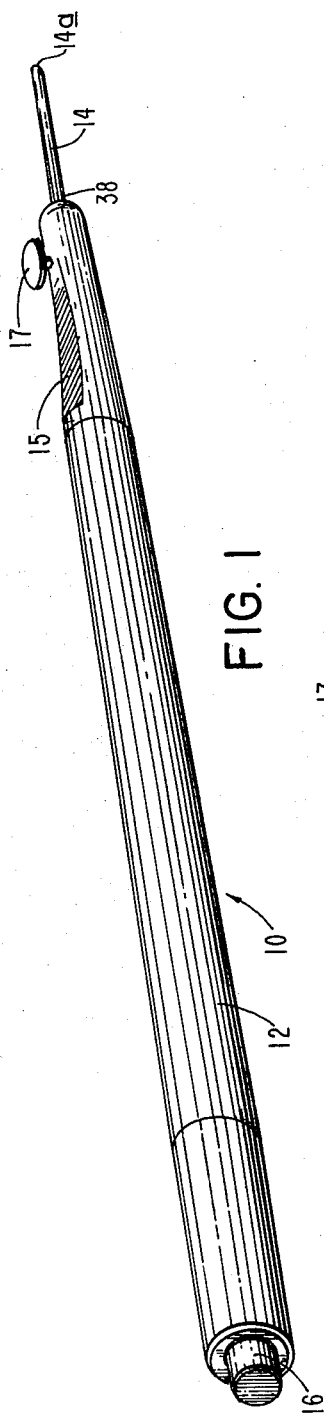
FIG. 1 is a perspective view of a defrostable, disposable cryosurgical probe made in accordance with this invention.

Referring first to FIG. 1 of the drawing, the probe shown generally at 10 is comprised of a pencil-like plastic housing 12 approximately 5.5 inches long and 0.4 inch in outside diameter. A tubular tip 14 projects from the distal end of the housing and the working end of the tip at 14a is closed. Shaped and roughened finger-engaging surfaces 15 are provided on the outside of the housing 12 near tip 14.

Probe 10 is activated by pressing a push button 16 protruding from its end opposite tip 14. In two to three seconds following depression of button 16, the probe tip 14a cools to the desired working temperature, e.g. $-30°$ C. In normal use the tip 14a will remain at that temperature for at least 3 to 5 minutes which is ample time to complete typical eye operations, such as a cataract extraction or removal of foreign material from the vitreous humor.

Upon completion of the surgical procedure, the doctor can depress a button 17 projecting from the housing near the probe tip which will cause the probe tip 14a to be warmed rapidly so that the probe tip can be separated from the tissue to which it is adhered in 2 to 3 seconds as opposed to the 8 to 15 seconds normally required by probes which do not have this rapid defrost capability.

Figure 2:
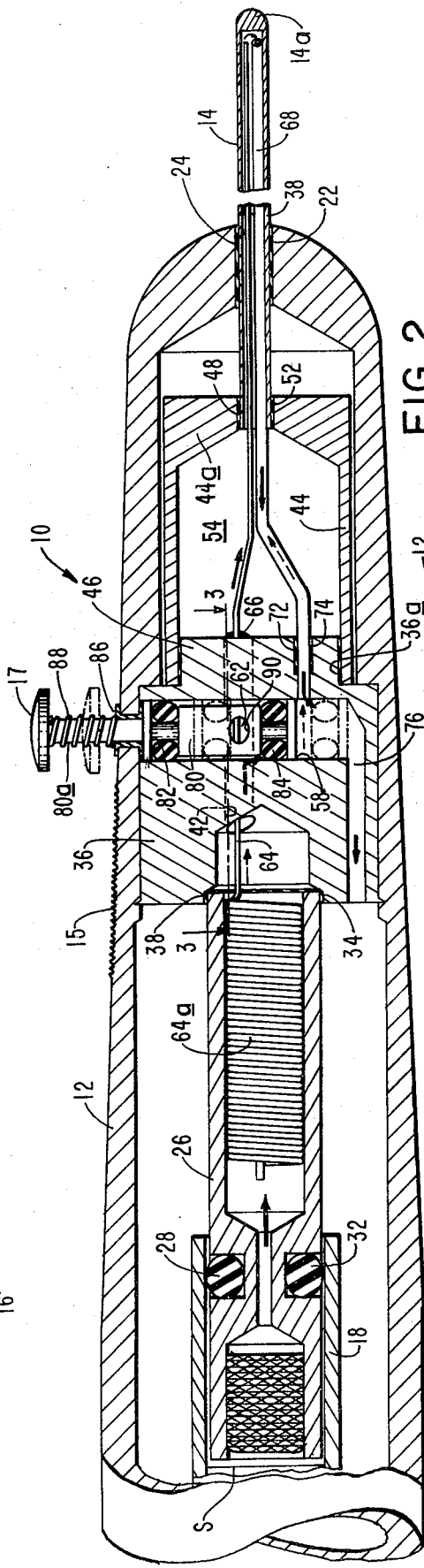
FIG. 2 is a fragmentary sectional view of the FIG. 1 probe on a larger scale.

Turning now to FIG. 2 of the drawing, housing 12 contains a cartridge 18 containing a supply of refrigerant, in this case, liquid Freon under suitable pressure, say, 75 psi at room temperature (72° F). Cartridge 18 is dimensioned so that it can shift axially in housing 12 when button 16 (FIG. 1) is depressed.

The probe tip 14 consists of a cylindrical stainless steel tube 0.062 inch in outside diameter which extends 0.5 inch from the housing. One end of the tube extends into housing 12 through an opening 22 provided therefor and is secured there by conventional means such as epoxy cement 24.

A tubular member 26 is positioned in housing 12 and has one end projecting into the end of the cartridge 18. The outer wall of member 26 is circumferentially grooved at 28 to accommodate an O-ring seal 32 which is positioned just inside the end of cartridge 18 to provide a fluid-tight sliding fit between member 26 and the inner wall of cartridge 18.

When button 16 is depressed, the cartridge 18 is urged toward member 26 causing that member to break a seal S in the cartridge permitting refrigerant to flow from the cartridge through member 26.

The opposite end of member 26 projects into an axial recess 34 in a valve manifold 36 situated inside housing 12. Member 26 is held in the recess by a suitable epoxy cement 38. Manifold 36 is generally cylindrical in shape and has a relatively small diameter passage 42 extending from the bottom of recess 34 axially to the opposite end of the manifold nearest probe tip 14. Positioned beyond manifold 36 in housing 12 is a cylindrical cup 44 whose rim is slid onto a necked-down portion 36a of manifold 36 and bonded thereto by epoxy cement 46. A passage 48 is formed in the end wall 44a of cup 44. Passage 48 receives the inner end of probe tip 14 which is bonded to the passage wall by suitable epoxy cement 52. Thus manifold 36 and cup 44 define a space 54 in the probe which is in direct communication with the interior of tip 14.

Figure 3:
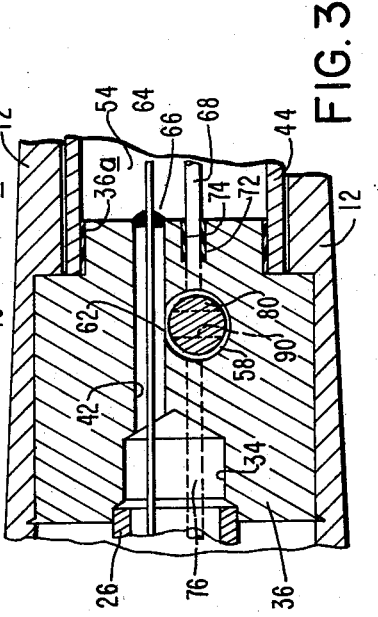
FIG. 3 is a sectional view along line 3—3 in FIG. 2.

Referring now to FIGS. 2 and 3, manifold 36 is formed with a transverse valve chamber 58 which extends from one side of manifold 36 almost to the opposite side of that manifold. Chamber 58 is slightly off center with respect to the longitudinal axis of the manifold so that one side of the chamber intersects the side wall of passage 42 through the manifold as best seen in FIG. 3 so that a small port 62 exists between passage 42 and chamber 58.

A small diameter capillary tube 64 extends from within tubular member 26, through manifold passage 42 and cup 44 down into the probe tip 14, terminating near its end 14a. Tube 64 has an inside diameter on the order of 0.004 inch and is on the order of 1 foot in length. Most of that tube length is contained as a relatively long small diameter coil 64a inside tubular member 26, the rest extending in a substantially straight line through space 54 into tip 14. The end of the manifold passage 42 at the point where the tube 64 emerges into space 54 is sealed by a suitable epoxy cement 66 so that any fluid in passage 42 cannot enter directly into the space 54 and tip 14.

A second length of tube 68 extends from manifold 36 into the probe tip 14 terminaing at a point near its outer end 14a. Tube 68 is larger in diameter than tube 64, and its end adjacent to the manifold connects to a passage 72 leading to the valve chamber 58 near the lower or closed end of that chamber. The tube 68 is held in place within passage 72 by suitable epoxy cement 74. A third passage 76 in manifold 36 extends from the end or bottom of the valve chamber 58 beyond passage 72 to the end of the manifold facing tubular member 26 where it opens into the space between the tubular member 26 and housing 12. That space is vented to the atmosphere through the crack around the button 16 (FIG. 1).

Referring to FIGS. 2 and 3, a generally cylindrical valve member 80 is slidably positioned inside chamber 58. Circumferential grooves are formed near the opposite ends of member 80 to accommodate O-ring seals 82 and 84 respectively which form fluid-tight sliding seals between the chamber 58 wall and the opposite ends of member 80. Member 80 has an integral stem 80a which projects from the open end of chamber 58 through an opening 86 in the side of housing 12, terminating in the push button 17 referred to in connection with FIG. 1.

Valve member 80 is movable between a solid line position shown in FIG. 2 which causes the probe to operate in its freeze mode and a dotted line position shown in that figure which causes the probe to operate in its defrost mode. Member 80 is normally maintained in its solid line position by a coil spring 88 encircling stem 80a and compressed between button 17 and the outer wall of housing 12 at the mouth of opening 86. The valve member is moved to its dotted line defrost position by depressing button 17. A transverse passage 90 through member 80 ensures equalized pressure around the member between seals 82 and 84.

When it is desired to activate the probe, the button 16 (FIG. 1) is depressed effecting the release of refrigerant from cartridge 18 as described above. The refrigerant flows through tubular member 26 and into the manifold passage 42 and thence through port 62 and into the portion of the valve chamber 58 between the O-ring seals 82 and 84 on the valve member which is normally raised as in FIG. 2. Since the opposite end of passage 42 is sealed by epoxy cement 66, the cartridge pressure is present in all the aforesaid spaces where refrigerant is present. Consequently the refrigerant remains as a liquid at room temperature in these spaces.

The liquid refrigerant inside tubular member 26 is, however, free to enter the open capillary tube 64 and flow through that tube into the probe tip 14 as indicated by the solid arrows in FIG. 2. As described above, the immersion of the inlet tube 64 in room temperature refrigerant ensures that the refrigerant flows through the tube 64 as a two phase fluid so that it rapidly cools tip 14. The refrigerant thereupon exhausts from the tip as a gas through the exhaust tube 68 and into the portion of the valve chamber 58 below seal 84 and thence passes to the atmosphere through the manifold exhaust passage 76 as shown by the solid arrows.

Following completion of the surgical procedure, when it is desired to release the probe tip from the tissue, button 17 is depressed causing the valve member 80 to assume its dotted line position in FIG. 2 in which the seal 84 on the valve member separates exhaust tube 68 and the exhaust passage 76. Immediately the liquid refrigerant in member 26 and passage 42 flows into passage 74 and tube 68 in the direction of the dotted line arrows, and floods the interior of tip 14 and the space 54. As mentioned previously, those regions form an enclosed space and the tube 68 has a relatively large diameter so that there is substantially no pressure drop imposed upon the refrigerant therein. Thus the refrigerant remains in its liquid phase at room temperature. The warm liquid inside tip 14 rapidly warms the working end of the tip thereby melting the tissue adhering to the tip and facilitating separation of the tip from the tissue. In actual practice, the tip end 14a warms sufficiently to effect separation within 2 to 5 seconds after the button 17 is depressed.

In the event the doctor wishes to operate the probe in its freeze mode again, he simply releases the button 17 allowing the valve member 80 to assume its FIG. 2 solid line position again. This immediately establishes communication between the interior of tip 14, exhaust tube 68 and the exhaust passage 76 leading to the atmosphere. Accordingly the liquid refrigerant inside probe tip 14 and inside space 54 immediately flashes to a vapor, cooling in the process and causing the working end of the tip 14a to recool to its operating temperature.

The probe can be cycled between its freeze and defrost modes of operation so long as the refrigerant supply lasts. Obviously the longer the doctor takes to accomplish the surgical procedure, the less refrigerant remains to effect subsequent defrost and freeze operations. However, should there be a need to pause during a particular operation, the refrigerant supply can be conserved by raising the tip of the probe as described in U.S. Pat. No. 3,910,278.

Thus the present disposable probe has all the advantages of the one described in the aforesaid patent in that it can operate for a relatively long period of time on a limited refrigerant supply. Further it is small, lightweight and easily manipulated by the doctor. Still, however, the present probe has a defrost capability which allows the probe tip to be separated quickly from tissue following completion of the operation. With all of these advantages, the probe is still of relatively simple construction, having only one valve member. Thus the probe is not appeciably more expensive than similar disposable probes having no defrost capability and less expensive than prior defrostable disposable probes. Accordingly it should find wide application in cryosurgery, particularly in connection with the treatment of eye problems.

It will thus be seen that the objects set forth above, among those made apparent from the preceding description, are efficiently attained, and since certain changes may be made in the above construction without departing from the scope of the invention, it is intended that all matter contained in the above description or shown in the accompanying drawing should be interpreted as illustrative and not in a limiting sense.

It is also understood that the following claims are intended to cover all the generic and specific features of the invention herein described.

We claim:
1. A cryosurgical probe comprising:
   A. a pencil-like housing;
   B. a pressurized liquid refrigerant-containing cartridge slidably positioned in the housing;
   C. a hollow thermally conductive tip projecting from one end of the housing;
   D. a valve manifold within the housing between the cartridge and the tip, said manifold defining a valve chamber;
   E. a first conduit between the cartridge and the manifold for conducting refrigerant as a liquid to the chamber;
   F. a second conduit extending through the first conduit for conducting refrigerant from the cartridge into the probe tip, said second conduit being bathed in the liquid refrigerant in the first conduit so that refrigerant flows through the second conduit into the probe tip as a two phase fluid;
   G. a third conduit extending from the valve chamber into the probe tip, said third conduit having a larger diameter than the second conduit;
   H. a fourth conduit extending from said chamber to the atmosphere; and
   I. a valve member movable within said chamber, said member having a portion projecting from said housing so that the valve member can be moved manually between.
      1. a first position in which the member connects the third and fourth conduits together and isolates those conduits from said first conduit so that said refrigerant flows into the probe tip through the second conduit and leaves the probe tip through the third and fourth conduits thereby cooling the tip, and
      2. a second position wherein the valve member connects the first and third conduits and isolates those conduits from said fourth conduit so that refrigerant flows into the tip through the third conduit as a liquid at room temperature thereby warming the tip.
2. The probe defined in claim 1 abd further including means accessible from without said housing for releasing refrigerant from said cartridge into said first and second conduits.
3. The probe defined in claim 2 wherein the releasing means comprise
   A. a penetrable seal in the cartridge;
   B. a means within the housing bearing against said seal; and,
   C. a push button projecting from said housing for shifting said cartridge axially in said housing against the bearing means whereby said bearing means open said seal thereby releasing the refrigerant from the cartridge.
4. A disposable probe comprising
   A. a housing;
   B. a hollow probe tip projecting from the housing;
   C. a pressurized, room-temperature, liquid refrigerant supply in the housing;
   D. a capillary tube for conducting refrigerant from the supply into the tip;
   E. a two position valve within the housing;
   F. an exhaust conduit of larger diameter than the capillary tube for conducting refrigerant between the tip and the valve;
   G. means for conducting liquid refrigerant from the supply to the valve;
   H. a vent conduit communicating between the valve and the atmosphere, and
   I. means accessible from without the housing for moving the valve between its two positions,
      1. in one of which positions said valve connects the exhaust conduit to the vent conduit whereby refrigerant flows into the tip through the capillary tube and exhausts from the tip through the exhaust and vent conduits expanding in the process and thereby cooling the tip, and
      2. in the other of which positions the valve connects the conducting means to the exhaust conduit and isolates the exhaust conduit from the vent conduit so that refrigerant from the supply flows through the exhaust conduit in reverse into the tip still under supply pressure and thereby floods the tip with room temperature refrigerant which warms the tip.

5. The probe defined in claim 4 wherein the capillary tube extends through the conducting means so that it is immersed in room temperature liquid refrigerant.

6. The probe defined in claim 5 wherein the capillary tube portion in the conducting means is in the form of a coil.

7. The probe defined in claim 4

A. wherein the supply has a penetrable seal upstream from the capillary tube, and
B. further including means acccessible from without the housing for opening said seal and releasing the refrigerant from the supply.

* * * * *